United States Patent [19]

Burton

[11] Patent Number: 4,735,697

[45] Date of Patent: Apr. 5, 1988

[54] METHOD AND APPARATUS FOR SEPARATING COMPLEX MIXTURES OF BIO-ORGANIC MATERIALS

[75] Inventor: William G. Burton, San Mateo, Calif.

[73] Assignee: Phoresis Transfer Systems, Inc., San Carlos, Calif.

[21] Appl. No.: 724,225

[22] Filed: Apr. 17, 1985

[51] Int. Cl.[4] ............................................. G01N 27/26
[52] U.S. Cl. ................................ 204/182.8; 204/182.9; 204/183.3; 204/299 R; 210/656; 435/803; 436/161
[58] Field of Search ............... 204/182.8, 182.7, 182.9, 204/183.3, 183.2, 299 R; 210/656; 435/803; 436/161

[56] References Cited

U.S. PATENT DOCUMENTS

| | | | |
|---|---|---|---|
| 3,384,564 | 5/1968 | Ornstein et al. | 204/182.9 |
| 4,061,561 | 12/1977 | Fletcher et al. | 204/299 R |
| 4,124,470 | 11/1978 | Dahms | 204/180.1 |
| 4,130,471 | 12/1978 | Grunbaum | 204/182.8 |
| 4,199,428 | 4/1980 | Hayashi et al. | 204/299 R |
| 4,204,929 | 5/1980 | Bier | 204/182.3 |
| 4,315,812 | 2/1985 | Karlson | 204/183.2 X |
| 4,323,439 | 4/1982 | O'Farrell | 204/299 R X |
| 4,375,401 | 3/1983 | Catsimpoolas | 204/301 |
| 4,396,477 | 8/1983 | Jain | 204/182.1 |
| 4,441,978 | 4/1984 | Jain | 204/301 |
| 4,452,901 | 6/1984 | Gordon et al. | 436/506 |
| 4,469,601 | 9/1984 | Beaver et al. | 210/658 |
| 4,642,169 | 2/1987 | Yoshisato et al. | 204/180.1 |

FOREIGN PATENT DOCUMENTS 3110804 9/1978 Fed. Rep. of Germany.
2840614 9/1978 Fed. Rep. of Germany.
56-119842 9/1981 Japan.

OTHER PUBLICATIONS

Chrambach, Andreas, The Practice of Quantitative Gel Electrophoresis, Appendix 2, pp. 225-233.
O'Farrell, P. H., The Journal of Biological Chemistry, (1975), vol. 250, No. 10, pp. 4007-4021.
Jovin, T. M., Biochemistry (1973), vol. 12, No. 5, pp. 871-898.
Laemmli, U. K., Nature (1970) vol. 227, pp. 680-685.

Primary Examiner—John F. Niebling
Assistant Examiner—W. T. Leader
Attorney, Agent, or Firm—Banner, Birch, McKie & Beckett

[57] ABSTRACT

A method and apparatus is described for separating complex mixtures of components, particularly bio-organic molecules, preferably on the basis of two independent physical characteristics. A sample initially is resolved in a first stage to yield a fluid stream containing the components of the sample longitudinally separated. The fluid stream then is aligned incident to the inlet face of a gel slab positioned in a electric field, having a field strength sufficient to force the separated and charged components from the flowing stream into the gel slab substantially simultaneously with exposure of said charged components to the electric field. Gel electrophoresis of the sample can then proceed in a known manner.

11 Claims, 3 Drawing Sheets

METHOD AND APPARATUS FOR SEPARATING COMPLEX MIXTURES OF BIO-ORGANIC MATERIALS

BACKGROUND OF THE INVENTION

1. Field of the Invention

The present invention broadly relates to a method and apparatus for conducting gel electrophoresis. The invention specifically relates to a method and apparatus for resolving a complex mixture of components into a fixed two-dimensional array of its constituents in a gel matrix. In its preferred form, the invention pertains to a method and apparatus for the separation of complex mixtures of bio-organic molecules such as proteins and nucleic acids on the basis of two independent physical characteristics.

2. Description of the Prior Art

At present, in order to obtain very high resolution in the separation of bio-organic molecules one generally must employ the technique of two-dimensional gel electrophoresis first described by P. H. O'Farrel, (1975) *Journal of Biological Chemistry*, 250:4007–4021). By utilizing this technique, exceedingly complex mixtures of bio-organic molecules, containing for example over 1,000 different proteins, are separated and analyzed at one time.

According to this delicate, labor-intensive and time-consuming procedure, components of a protein mixture are separated in a two-step procedure which first involves a partition of proteins as a function of net surface charge by isoelectric focusing (IEF) in one dimension, followed by separation as a function of size (by molecular sieving) in a second dimension.

This separation process is carried out in a jelly-like material called a polyacrylamide gel. This gel is cast by polymerization of a mixture of acrylamide monomer and an appropriate cross-linking agent, such as N,N,N',N'-tetramethylethylene-diamine (TEMED), in suitably sized glass tubes or between rectangular glass plates to form rods or thin sheets, respectively.

Isoelectric focusing (IEF), the first separation step, relies on the fact that bio-organic molecules such as proteins and peptides, are three-dimensional objects with ionizable surface groups (e.g., carboxyl, amino, imidazole, guanidinium, etc.). These ionizable groups are amphoteric in nature; i.e., below a certain pH, such groups are positively charged and above a certain pH, they are negatively charged. At a particular pH value, called the isoelectric point (pI), the number of positively charged surface groups equals the number of negatively charged surface groups on the molecule. Consequently, the molecule will have a net charge of zero.

IEF involves the electrophoretic migration of a molecule in a pH gradient until it reaches the pH corresponding to its isoelectric point. As the net charge of the molecule is zero at that point, it becomes immobilized and remains "focused" at its respective pI.

Stable pH gradients are generated within polyacrylamide gels by inclusion of specialized buffer constituents called ampholytes. Ampholytes consist of a mixture of low molecular weight amphoteric compounds with isoelectric points covering a defined range of pH values. Application of a constant-voltage, DC electric field to an ampholyte-buffered gel causes the ampholytes to focus according to their pIs, thereby establishing a pH gradient with sufficient buffering capacity and conductance for subsequent focusing of amphoteric macromolecules.

After performing the first dimension IEF separation in a gel, cast in a glass tube, the technician performing the separation then must carefully remove the gel rod, which contains the focused proteins, from the glass tubing.

Typically, each gel rod then is treated with a second dimension electrophoresis buffer solution. This aqueous buffer solution contains a detergent such as sodium dodecyl sulfate (SDS), which binds to proteins in the gel providing these macromolecules with a net negative charge. Afterwards, each gel sample is placed on top of and cemented to one edge of a second dimension polyacrylamide gel slab.

The assembled composite consisting of the treated first dimension gel overlaying and secured to the second dimension gel slab then is placed within an electric field between appropriate electrically conductive buffer solutions and separation in the second dimension may proceed on the basis of the proteins' differing molecular sizes via the process of molecular sieving.

Depending upon the particular apparatus design and gel and buffer chemistries, the technique of two-dimensional gel electrophoresis requires anywhere from about 17 hours to more typically about 30 hours to perform each separation. Moreover, not only is this separation procedure quite labor-intensive and time-consuming, but as those skilled in this technology readily appreciate the procedure also demands very high expertise and exacting laboratory techniques on behalf of each operator to ensure reproducibility of results. Unavoidably, the technique also places the fragile polyacrylamide gel containing the separated components generated in the first dimension at considerable risk during the transfer process preparatory to the second dimension separation.

As a consequence of these substantial drawbacks, two-dimensional gel electrophoresis has not been used for many applications where the procedure is ideally suited, such as for example clinical diagnostic screening and other large scale analytical applications.

Another separation technique useful for separating bio-organic molecules which continues to receive considerable attention from both the basic researcher and clinical diagnostician is high performance liquid chromatography (HPLC). Although incapable of achieving the same degree of resolution possible with two-dimension gel electrophoresis, this procedure nevertheless provides a very high resolution of the components in a complex mixture. In fact, recent advances in this separation technology have virtually eliminated the gap between this technique and one-dimensional electrophoresis techniques. More importantly, when using this technology the separation of complex mixtures of bio-organic molecules is achieved in only a fraction of the time necessary to carry out the process of gel electrophoresis.

According to this technique, a mobile phase or eluate, into which the sample to be analyzed has been injected, is forced through a bed of microparticulate chromatographic packing material at a relatively high linear velocity. Velocities on the order of 0.1 millimeter/second or greater are typical. As recognized by those skilled in this art, separation of components in the sample depends in large part upon eluate chemistry and the nature of the packing material used. Proteins and other bio-organic molecules are separated in this procedure, inter alia, on the basis of size (gel permeation chromatography), ionic properties (ion-exchange), absorptive characteristics (absorption chromatography) and hydrophobicity (reversed phase chromatography).

Analysis of the separated components typically is accomplished using in-line detectors measuring such component properties as absorbance and refractive index. It also is known to couple the detector and the chromotagraphic column through a post-column reactor wherein separated components of the sample are converted, by reaction with appropriate reagents, into fluorescent or color derivatives. The so-altered species then can be identified using an appropriate detector.

One object of the present invention is to provide a method and apparatus for automating gel slab electrophoresis.

Another object of the present invention is to provide a method and apparatus suitable for sequentially resolving a complex mixture of components and particularly a mixture of bio-organic molecules, preferably according to two independent physical characteristics.

A further object of this invention is to provide a method and apparatus for separating a complex mixture of components, particularly a mixture of bio-organic molecules, which method and apparatus exhibit advantages of both high performance liquid chromatography and two dimensional gel electrophoresis techniques.

Yet a further object of this invention is to provide method and apparatus which automate the sequential separation of a complex mixture of components, particularly a mixture of bio-organic molecules, that has heretofore been accomplished using the well-known manual procedure of two-dimensional gel electrophoresis, without losing the resolving power inherent in such well-known technique.

These and other objects of this invention will become apparent from a consideration of the specification and appended claims.

SUMMARY OF THE INVENTION

In a first aspect, the present invention broadly relates to a method for loading the components of a sample mixture into an electrophoresis gel slab which comprises:

(a) forming said sample into a flowing stream of fluid, (b) treating said flowing stream of fluid, as required, so that the components in said flowing stream exhibit a substantially uniform surface charge density; and (c) aligning the flow of said stream containing said charged components incident to an inlet face of a gel slab by moving a source of said flow relative to the inlet face of said gel slab, said gel slab being positioned in an electric field having a sufficient field strength to force said charged components from said stream into said gel slab substantially simultaneously with exposure of said charged components to said electric field.

In another aspect, the present invention comprises a method for separating the components of a sample mixture comprising:

(a) treating said sample so as to generate a treated fluid sample having its components longitudinally separated on the basis of a common physical characteristic of said components;

(b) recovering said treated fluid sample as a flowing steam of fluid;

(c) treating said flowing stream, as required, so that the longitudinally separated components in said flowing stream exhibit a substantially uniform surface charge density, said treatment being accomplished with substantially no loss in the separation obtained in step (a);

(d) aligning the flow of said stream containing said longitudinally separated and charged components incident to an inlet face of a gel slab by moving a source of said flow relative to the inlet face of said gel slab, said gel slab being positioned in an electric field having a sufficient field strength to force said charged components from said stream into said gel slab with substantially no loss of the separation obtained in step (a) substantially simultaneously with exposure of said longitudinally separated and charged components to said electric field; and (e) resolving said components in said gel slab on the basis of a common physical characteristic of said components.

Preferably, separation of the components in the sample in steps (a) and (e) is on the basis of two independent physical characteristics.

In a third aspect, the present invention comprises an apparatus for loading the components of a sample mixture into an electrophoresis gel slab comprising:

(a) first conduit means for transfering said sample mixture as a flowing stream of fluid;

(b) associated pump and mixer means for treating said flowing stream transferred in said first conduit means with a reagent stream so that the components in said flowing stream exhibit a substantially uniform surface charge density;

(c) a gel slab suitable for gel electrophoresis;

(d) second conduit means for conducting said flowing stream of said charged components to a gel tracking carriage assembly;

said gel tracking carriage assembly positioned over an inlet face of said gel slab and adapted for movement along the inlet face of said gel slab, said gel tracking carriage assembly including an outlet nozzle for aligning said flowing stream containing said charged components incident to said inlet face, the end of said nozzle being closely spaced from and oriented substantially parallel to the inlet face of said gel slab and (f) means for generating an electric field in said gel slab having a sufficient field strength to force said charged components from said flowing stream into said gel slab substantially simultaneously with exposure of said charged components to said electric field.

In a fourth aspect, the present invention also comprises an apparatus for separating the components of a sample mixture comprising:

(a) column means for longitudinally separating the components in a fluid sample on the basis of a common physical characteristic of said components;

(b) first conduit means for recovering a treated fluid sample from said column as a flowing stream of fluid;

(c) associated pump and mixer means for treating said flowing stream recovered in said first conduit means with a reagent stream so that the separated components in said flowing stream exhibit a substantially uniform surface charge density, said associated pump and mixer means accomplishing said treatment with substantially no loss in the separation of said components;

(d) a gel slab suitable for gel electrophoresis;

(e) second conduit means for conducting said flowing stream of said longitudinally separated and charged components to a gel tracking carriage assembly;

said gel tracking carriage assembly positioned over an inlet face of said gel slab and adapted for movement along the inlet face of said gel slab said gel tracking carriage assembly including an outlet nozzle for aligning said flowing stream containing said longitudinally separated and charged components incident to said inlet face, the end of said nozzle being closely spaced from and oriented substantially parallel to the inlet face of said gel slab, and (f) means for generating an electric field in said gel slab having a sufficient field strength to force said charged components from said flowing stream into said gel slab with substantially no loss in the longitudinal separation of said components substantially simultaneously with exposure of said longitudinally separated and charged components to the electric field.

BRIEF DESCRIPTION OF THE DRAWINGS

FIG. 4, in particular, is an enlarged view of the outlet nozzle and inlet face of the gel slab.

DETAILED DESCRIPTION

Figure 1:
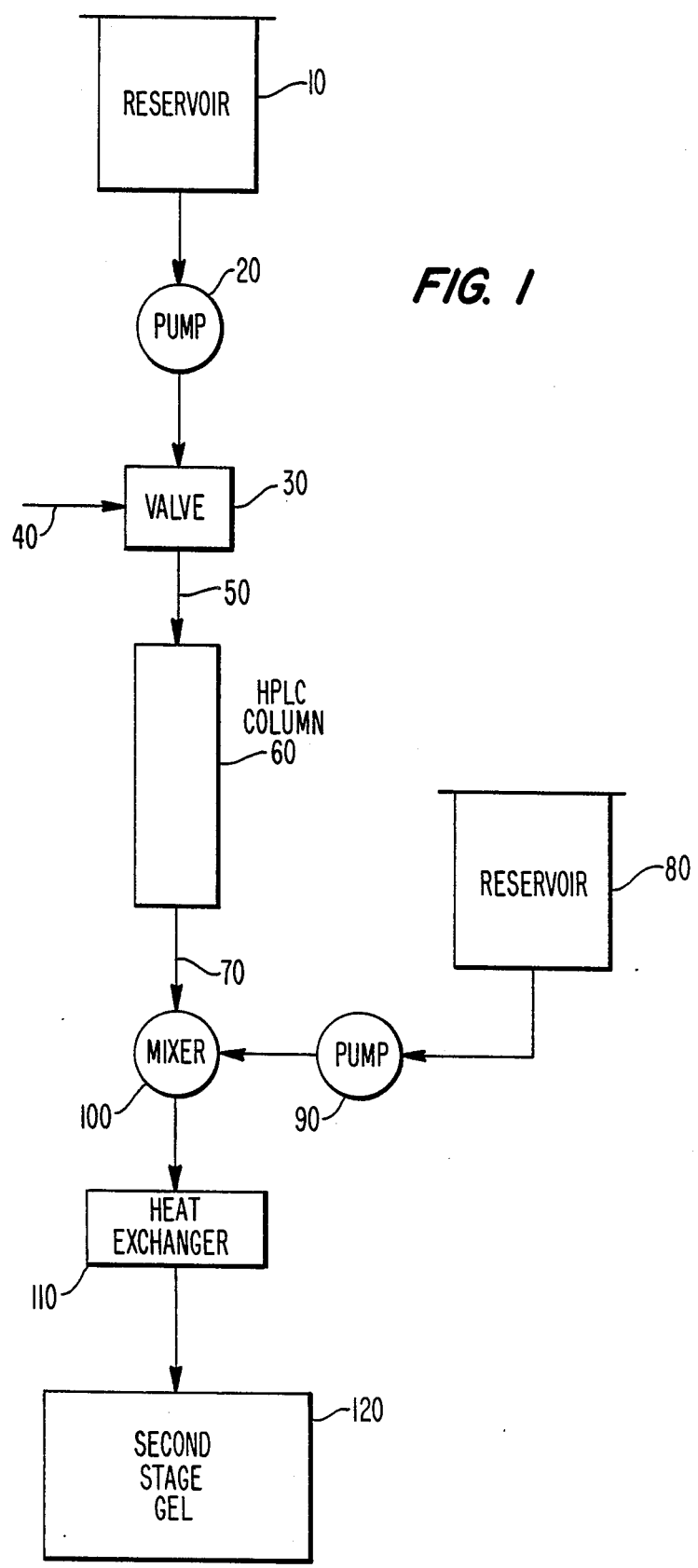
FIG. 1 is a schematic illustration of apparatus useful for carrying out the preferred method of this invention.

The present invention pertains to a method and apparatus suitable for separating complex mixtures of components such as bio-organic molecules, particularly including proteins or nucleic acids, preferably on the basis of two independent physical characteristics of said components. FIG. 1 schematically illustrates one embodiment for carrying out the method of this invention.

In this particular embodiment, a high performance liquid chromatography column 60 is used to effect the first stage separation. As shown in FIG. 1, an isocratic elution stream obtained from reservoir 10 is pumped through a sample injection valve 30 using a high pressure, low impulse, constant flow pump 20 such as the Beckman Instruments Model 114M Solvent Delivery System. The sample containing the mixture of components to be separated is injected into the sample injection valve 30 through conduit 40 and is carried by the elution stream into the HPLC column 60 through conduit 50. As will be appreciated by those skilled in this technology, an elution stream composition must be selected which does not interfere with the second stage separation (electrophoresis). Appropriate compositions can be obtained using routine experimentation.

The actual design of the HPLC column and the particular microparticulate packing employed forms no part of the present invention. Any of the wide variety of commercially available hardware could be used in concert with microparticulate column packing materials such as the Pharmacia Fine Chemicals MonoBead (TM) line of chromatographic adsorbents specifically designed for peptide and protein chemistry. In HPLC column 60, different components in the sample are separated longitudinally from one another on the basis of a common physical characteristic or characteristics such as for example size, ionic or absorptive characteristics, hydrophobicity or a combination thereof. As the elution stream continues to be pumped from reservoir 10 different components in the originally injected sample move through the column bed at different velocities as a consequence of such different property(ies) thereby causing these components to separate. The components in the original sample appear as longitudinally spaced chromatographic waves or bands in the fluid stream or treated fluid sample (generally a liquid) flowing out of the HPLC column in conduit 70. The treated fluid sample containing the longitudinally separated components is recovered as a continuously flowing stream of fluid in conduit 70.

Figure 2:
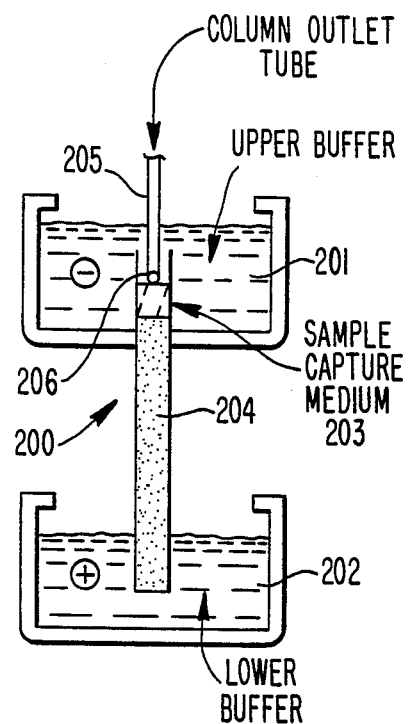
FIGS. 2-4 illustrate the outlet nozzle of the gel tracking carriage assembly in relation to the inlet face of the electrophoresis gel slab.
Figure 3:
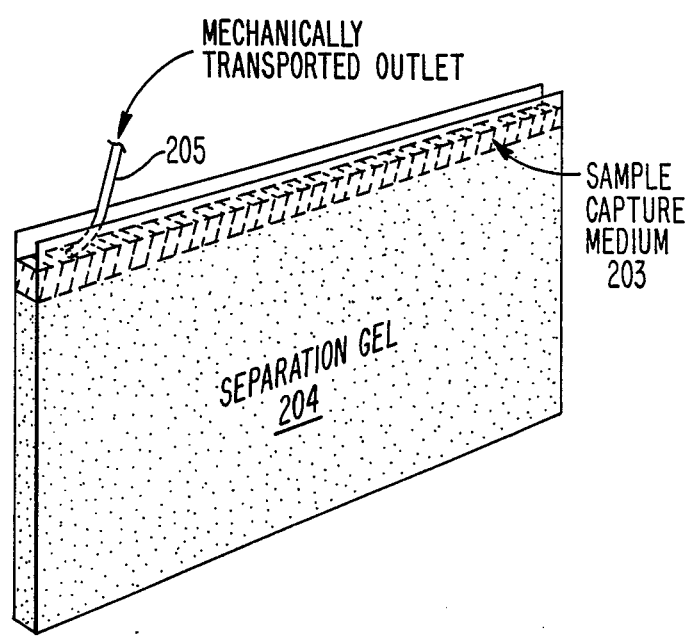

In the second stage separation, the longitudinally separated components then are resolved in a direction orthogonal to the separation obtained by the first stage separation. As shown in FIG. 1 embodiment, this separation is accomplished by gel electrophoresis, preferably using a controlled porosity polyacrylamide gel material. In the broad practice of this invention, the second stage gel electrophoresis may be run using any gel medium conventionally employed, such as polyacrylamide. Preferably, as shown in FIGS. 2 and 3, the gel slab consists of two gel phases a stacking gel (capture medium) and a separating gel, such composites are well-known to those skilled in this technology and require no further description.

Before entering the second stage separation the longitudinally separated components obtained in the first dimension separation are treated, as required, so that the components exhibit a substantially uniform net surface charge density. For example, treatment generally is required if a protein-containing sample is being separated. Treatment generally would not be required if a mixture of nucleic acids was being separated.

Proteins are relatively large bio-organic molecules composed of large numbers of amino acids residues. Proteins assume exceedingly complex conformations, and generally do not exhibit a uniform surface charge density in aqueous medium. Consequently, in order to effectuate further separation of the proteins in the second stage gel matrix it is necessary to treat the proteins so as to produce a uniform charge environment.

A uniform surface charge density can be imposed in a satisfactory manner on the protein components by using any of a variety of protein denaturing solutions well-known in the art, e.g., the detergent sodium dodecyl sulfate (SDS), and the reducing agent 2-mecaptoethanol. In the FIG. 1 embodiment, this treatment is accomplished by pumping a denaturing solution from reservoir 80 using constant flow, low pulse output pump 90 into mixer 100 where the denaturing solution is blended with the continuously flowing stream of the treated fluid sample containing the longitudinally separated components. The denaturing solution stream is blended into the treated fluid sample in a manner which does not substantially degrade the resolution obtained in the first dimension HPLC separation. The detergent component of the denaturing solution (e.g., SDS) coats the protein components in the treated sample so as to yield a uniform charge per unit mass environment. The treated fluid sample then can be passed through a heat exchanger 110, if necessary, to activate the detergent-protein interaction. The sample processing steps carried out by means of the mixer 100 and heat exchanger 110 can be achieved by a wide variety of commercially available post-column reactors such as the Beckman Instruments Model 230 system.

The continuously flowing stream now containing longitudinally separated and charged components then is passed to the second stage gel 120. The separation in the second stage is accomplished on the basis of the differing sizes of the longitudinally separated components of the fluid sample. As recognized by one skilled in this technology, the resolution obtained in the second stage separation requires use of a gel matrix material having a pore size controlled to approximate the size of the components being separated. In this way, molecular sieving occurs and separation in the gel occurs on the basis of molecular size. Preferably, the first stage separation was accomplished on the basis of an independent physical characteristic.

Figure 4:
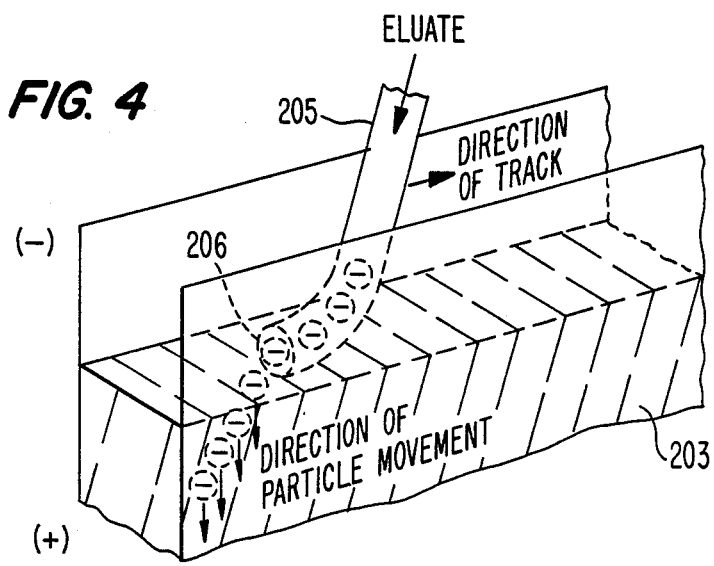

Referring now to FIGS. 2 through 4, the procedure for transferring the longitudinally separated and charged components in the continuously flowing stream to the second stage gel slab is illustrated. As shown in FIG. 2, a gel slab 200 is interposed in an electric field (D.C.) having opposite edges in contact with appropriate electrically conductive buffer solutions 201 and 202. The continuously flowing stream preferably having a density equal to or greater than the density of the upper buffer solution, is aligned incident to the inlet face of the gel slab by flowing the treated stream through an appropriately configured outlet nozzle 205 of a gel tracking carriage assembly (not shown) and simultaneously moving the gel tracking carriage assembly along the inlet face of the gel slab. As shown, the inlet face of the gel slab comprises a stacking gel or capture medium 203, which overlays the separating gel 204. The outlet 206 of the nozzle 205 is oriented substantially parallel to and positioned in close proximity to the inlet face of the gel slab (e.g., about 0.1 to 0.5 mm above the face of the gel slab).

The gel tracking carriage assembly traverses the inlet face of the gel slab at a rate coordinated with the total time required for longitudinal separation of the sample components in the first stage separation. Means for moving the gel tracking carriage assembly across the face of the gel slab in coordination with the total time required for the first stage separation, including the necessary motive means and carriage assembly, will be apparent to those skilled in the art. In this way the longitudinally separated components are aligned incident to the entire length of the inlet face of the gel slab. By maintaining an electric field across the gel slab of a sufficient field strength, the longitudinally separated and charged components in the fluid stream are forced directly from the fluid sample stream into the gel slab substantially simultaneously with the exit of said stream from the outlet nozzle and exposure of the separated and charged components to the electric field such that there is substantially no loss in the separation (resolution) obtained in the first stage. This process is schematically illustrated in FIG. 4.

The direct current power requirements for loading the separated components of the treated fluid sample into the gel slab typically will be on the order of about 25 watts. The same (or different) requirements then can be used to perform the second stage electrophoresis separation. An appropriate power for conducting specific separations can be determined using routine experimentation. Apparatus available in the prior art for imposing an electrical field across a gel slab and for cooling the gel slab, if required, during operation, such as the Pharmacia Model GE-2/4 Vertical Slab Gel Electrophoresis unit can be used in practicing the present invention.

By this arrangement, the resolution achieved in the first stage separation is preserved substantially completely upon the transfer of the sample to the second stage separation.

As shown more clearly in FIG. 3, the inlet face of the separation gel preferably is provided with a different gel chemistry (pore structure and electrolyte buffer composition), to maximize the rate that the charged components of the treated fluid sample are driven into the second stage gel. Such gel electrolyte systems, described as multiphasic zone electrophoresis systems (cf. T. M. Jovin, *Biochemistry* 12: 871-898), are known in the prior art. One such gel chemistry system is that of U. K. Laemmli (*Nature* 227: 680-685[1970]. Gels of this type are preferred for use in the present invention.

After loading the charged components of the fluid sample into the inlet face of the second stage gel slab, the gel now is ready for initiation of the second stage electrophoretic separation. This separation can be conducted immediately after loading the sample components into the gel or, if desired, the gel can be stored under appropriate conditions and the separation conducted at a latter time together with numerous other gels prepared in a similar fashion. The option of storing numerous gels for later separation en masse is an important advantage of the present invention.

Once the second stage electrophoteric separation is complete, visualization or recovery of the separated components in the gel slab can be accomplished for example using standard techniques of colorimetry, radiology and extraction.

In the broad practice of this invention, any procedure for separating components in a fluid, e.g., liquid, sample in a longitudinal fashion so as to produce a continuously flowing stream of fluid can be used for the first stage separation. As used throughout the specification and claims, the term "longitudinal" broadly refers to the process of separating a mixture of components in a fluid, e.g., liquid, sample into a treated sample that contains a one-dimensional spaced array of said components. The term "longitudinal" is not used to characterize the uniformity of the spacing between individual separated components but rather is used in a broader sense to emphasize the nature of the separation, that is that the separation is accomplished in a single dimension. While any of the wide variety of HPLC techniques preferably are used for the first stage separation, the present invention also contemplates using other available techniques for longitudinally separating components in a fluid stream, such as any of the known electrophoresis techniques. The necessity of generating a fluid stream, of course, excludes gel electrophoresis for the first stage separation however.

Figure 5:
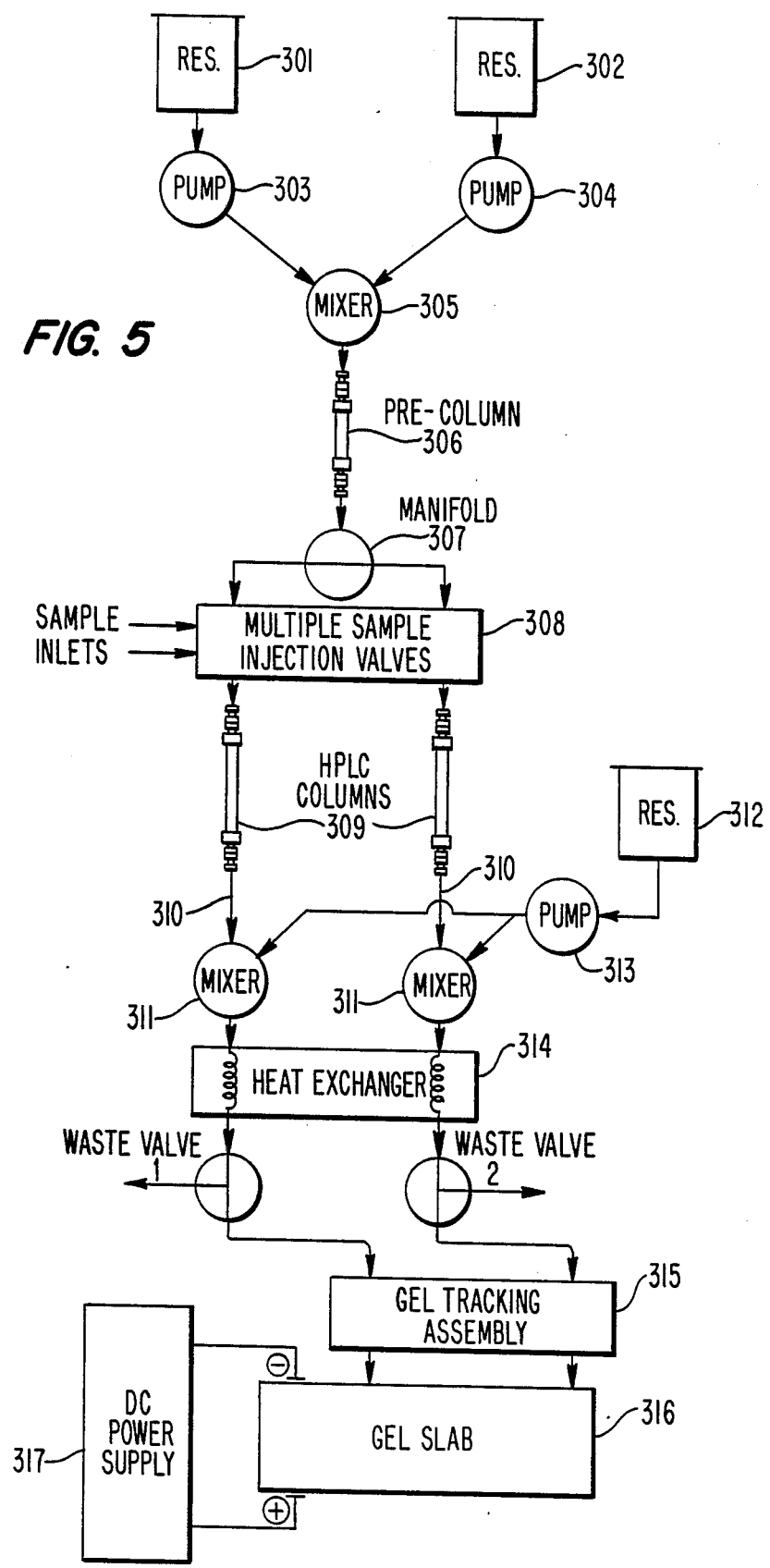
FIG. 5 schematically illustrates another apparatus useful for practicing a preferred embodiment of the method of the present invention.

Referring next to FIG. 5, a preferred embodiment for carrying out the method of the present invention is schematically illustrated. The major elements of this preferred arrangement include an array of HPLC columns for conducting the first stage separation; the equipment needed to prepare the output of the first stage separation for the second stage gel electrophoresis separation including the reagent supply and the necessary pumps, mixers and heat exchange equipment, and the second stage electrophoresis gel arrangement including the gel itself, the gel tracking carriage assembly for loading the output of the first stage separation on the gel and the means for generating an electric field (D.C.).

As in the FIG. 1 embodiment, the preferred procedure for conducting the first stage separation is high performance liquid chromatography. In the FIG. 5 embodiment, however, this separation is accomplished by using gradient elution. As shown, the elution stream for the first stage separation is prepared by blending a portion of the elution solvent in reservoir 301 with a portion of the elution solvent in reservoir 302 both fed to mixer 305 using pumps 303 and 304, respectively. By separately controlling the pumping rates of pumps 303 and 304 any of a wide range of continuous and discontinuous elution gradients can be prepared. As is known in the prior art, the composition of elution solvents in reservoir 301 and 302 are constrained by the electrolyte combinations used for carrying out the second stage electrophoresis operation as specified by the Multiphasic Buffer Systems Output developed by T. M. Jovin, M. L. Dante and A. Chambrach, available as documents PB No. 196085 to 196092 and 203016 from the National Technical Information Service, Springfield, Va.

The mixed eluate stream so-prepared then is passed through a pre-column 306 for removing any solvent impurities. The elution stream is introduced into a manifold 307 which partitions the elution stream prior to its entry into the multiple sample injection valves 308 for flow into the parallel array of HPLC columns 309. In this arrangement, multiple samples, e.g., blood serum samples from a large number of patients, are separately injected into each partitioned elution stream and each sample then is delivered to its respective HPLC column.

As in the FIG. 1 embodiment, as each elution stream flows through its respective HPLC column, different components in the injected sample tend to move at different rates through the chromotographic bed as a consequence of their different properties, causing the components to be longitudinally separated. The fluid stream containing the longitudinally separated components then flows from each HPLC column 309 through conduits 310 to an associated mixing device 311 where a reagent stream, e.g., SDS, obtained from reservoir 312, necessary to yield a uniform surface charge density on the separated components in the fluid stream is blended with the longitudinally separated sample. The reagent stream is fed to the respective mixers 311 from reservoir 312 using pump 313. Each continuously flowing stream then passes through heat exchanger 314 to activate the reagent and complete the binding of SDS to the separated components in the treated fluid.

Each treated fluid stream then is passed to the gel tracking assembly 315 and the treated components of each fluid stream are aligned incident to an inlet face of a gel slab, indicated schematically as element 316, as described in connection with the FIG. 1 embodiment. Each gel is exposed to a D.C. field generated using power supply 317. Using this arrangement, multiple samples can be separated on the basis of two independent physical characteristics using gel electrophoresis in only a fraction of the time required in the prior art.

In this preferred embodiment a micro-processor typically will provide a complete sequence of operations needed to process samples through the first and second stage separations, including the generation of the elution gradient for the first stage separation, sample injection, treatment of the first stage output with reagent and controlling the gel tracking carriage assembly and power supply for transfering the treated first stage output into the second stage gel slab by electromotive force.

In the practice of the present invention, a wide variation in the procedures for conducting the various steps of the inventive method are possible. For example, in addition to using high performance liquid chromatography for the first stage separation, the present invention also contemplates the use of electrophoresis such as isoelectric focussing using pH gradient and density gradient techniques.

While the present invention has been described with respect to preferred embodiments and particularly to the separation of the components in a complex mixture, it should be understood that various changes may be made without departing from the spirit and scope of the invention as particularly claimed below. For example, another aspect of this invention relates to the method and apparatus for loading the components of a sample into an electrophoresis gel slab.

I claim:

1. A method for separating the components of a sample mixture comprising:
   (a) treating said sample mixture so as to generate a treated fluid sample having its components longitudinally separated on the basis of a common physical characteristic of said components;
   (b) recovering said treated fluid sample as a continuously flowing stream of fluid;
   (c) treating said continuously flowing stream, as required, so that the longitudinally separated components in said continuously flowing stream exhibit a substantially uniform surface charge density, said treatment being accomplished with substantially no loss in the separation obtained in step (a);
   (d) aligning the continuously flowing stream containing said longitudinally separated components exhibiting a substantially uniform surface charge density incident to an inlet face of a gel slab, said inlet face in contact with a conductive buffer solution, by moving a source of said continuously flowing stream relative to the inlet face of said gel slab, said flowing stream having a density equal to or greater than the density of said conductive buffer solution and said gel slab being positioned in an electric field having a sufficient field strength to force said components exhibiting a substantially uniform surface charge density from said continuously flowing stream into said gel slab with substantially no loss of the separation obtained in step (a) substantially simultaneously with exposure of said longitudinally separated components exhibiting a substantially uniform surface charge density to said electric field;
   (e) forcing said components into said gel slab; and
   (f) resolving said components in said gel slab on the basis of a common physical characteristic of said components.

2. The method of claim 1 wherein said gel slab comprises a stacking gel overlaying a separating gel.

3. The method of claim 2 wherein the separating gel is composed of polyacrylamide.

4. The method of claim 1 wherein said common physical characteristic is selected from the group consisting of size, ionic character, absorption affinity and hydrophobicity.

5. The method of claim 1 wherein the common physical characteristic of step (e) is size.

6. The method of claim 5 wherein the common physical characteristic of step (a) is different from the common physical characteristic of step (e).

7. The method of claim 6 wherein step (a) comprises high performance liquid chromatography.

8. The method of claim 2 wherein said flowing stream is mixed with a protein denaturing solution as said treatment in step (c).

9. The method of claim 8 wherein said solution contains sodium dodecyl sulfate.

10. The method of claim 8 wherein said solution contains 2-mecaptoethanol.

11. An apparatus for separating the components of a sample mixture comprising:

(a) column means for longitudinally separating the components in a fluid sample on the basis of a common physical characteristic of said components;

(b) first conduit means for recovering a treated fluid sample from said column means as a continuously flowing stream of fluid;

(c) associated pump and mixer means for treating said continuously flowing stream recovered in said first conduit means with a reagent stream to apply a substantially uniform surface charge density to the separated components in said continuously flowing stream, said associated pump and mixer means accomplishing said treatment with substantially no loss in the separation of said components;

(d) a gel slab suitable for gel electrophoresis;

(e) second conduit means for conducting said continuously flowing stream of said longitudinally separated components exhibiting a substantially uniform surface charge density from said pump and mixer means to a gel tracking carriage assembly;

said gel tracking carriage assembly positioned over an inlet face of said gel slab and adapted for movement along the inlet face of said gel slab, said gel tracking carriage assembly including an outlet nozzle for aligning said continuously flowing stream containing said longitudinally separated components exhibiting a substantially uniform surface charge density incident to said inlet face, the end of said nozzle being closely spaced from and oriented substantially parallel to the inlet face of said gel slab, and (f) means for generating an electric field in said gel slab having a sufficient field strength to force said components exhibiting a substantially uniform surface charge density from said continuously flowing stream into said gel slab with substantially no loss in the longitudinal separation of said components substantially simultaneously with exposure of said longitudinally separated components exhibiting a substantially uniform surface charge density to the electric field.

* * * * *